(12) United States Patent
Koivisto et al.

(10) Patent No.: US 9,872,638 B2
(45) Date of Patent: Jan. 23, 2018

(54) METHOD AND APPARATUS FOR DETERMINING INFORMATION INDICATIVE OF CARDIAC MALFUNCTIONS

(71) Applicant: TURUN YLIOPISTO, Turku (FI)

(72) Inventors: Tero Koivisto, Turku (FI); Tuomas Valtonen, Turku (FI); Mikko Pankaala, Raisio (FI); Kati Sairanen, Naantali (FI)

(73) Assignee: PRECORDIOR OY, Turku (FI)

( * ) Notice: Subject to any disclaimer, the term of this patent is extended or adjusted under 35 U.S.C. 154(b) by 0 days.

(21) Appl. No.: 14/899,782

(22) PCT Filed: Jun. 13, 2014

(86) PCT No.: PCT/FI2014/050477
§ 371 (c)(1),
(2) Date: Dec. 18, 2015

(87) PCT Pub. No.: WO2014/202829
PCT Pub. Date: Dec. 24, 2014

(65) Prior Publication Data
US 2016/0135717 A1    May 19, 2016

(30) Foreign Application Priority Data

Jun. 19, 2013   (FI) ...................... 20135669

(51) Int. Cl.
*A61B 5/04* (2006.01)
*A61B 5/11* (2006.01)
(Continued)

(52) U.S. Cl.
CPC ............ *A61B 5/1102* (2013.01); *A61B 5/046* (2013.01); *A61B 5/0456* (2013.01);
(Continued)

(58) Field of Classification Search
CPC .... A61B 5/1102; A61B 5/04525; A61B 5/721
See application file for complete search history.

(56) References Cited

U.S. PATENT DOCUMENTS 5,558,097 A * 9/1996 Jacobson ............. A61N 1/3702
600/518
8,251,911 B2    8/2012 MacQuarrie et al.
(Continued)

FOREIGN PATENT DOCUMENTS

WO    2008-095318    8/2008

OTHER PUBLICATIONS

FI search report, dated Apr. 4, 2014; Application No. 20135669.
(Continued)

*Primary Examiner* — Eric D. Bertram
(74) *Attorney, Agent, or Firm* — Young & Thompson (57) ABSTRACT

An apparatus for determining information indicative of cardiac malfunctions includes a processing device (602) configured to detect whether the time-trend of a signal indicative of cardiovascular motion manifests an indicative phenomenon where the amplitude of a first heartbeat is greater than the amplitude of a second heartbeat and the temporary heartbeat rate is greater prior to the first heartbeat than prior to the second heartbeat. The processing device is further configured to produce an indicator of cardiac malfunction, e.g. an indicator of atrial fibrillation, in response to a situation in which the indicative phenomenon is detected to be present.

29 Claims, 7 Drawing Sheets

(51) Int. Cl.
*A61B 5/046* (2006.01)
*A61B 5/0452* (2006.01)
*A61B 5/0456* (2006.01)
*A61B 5/00* (2006.01)

(52) U.S. Cl.
CPC ........ *A61B 5/04525* (2013.01); *A61B 5/6804* (2013.01); *A61B 5/686* (2013.01); *A61B 5/6898* (2013.01); *A61B 5/1107* (2013.01); *A61B 5/7275* (2013.01); *A61B 2562/028* (2013.01); *A61B 2562/0219* (2013.01)

(56) References Cited

U.S. PATENT DOCUMENTS

| | | | |
|---|---|---|---|
| 8,255,042 | B2 | 8/2012 | MacQuarrie et al. |
| 2003/0233034 | A1 | 12/2003 | Varri et al. |
| 2008/0300641 | A1* | 12/2008 | Brunekreeft ....... A61B 5/02405 607/6 |
| 2009/0112106 | A1 | 4/2009 | Zhang |
| 2011/0118614 | A1 | 5/2011 | Brauers et al. |
| 2011/0301480 | A1* | 12/2011 | Ghanem .............. A61B 5/0452 600/516 |

OTHER PUBLICATIONS

Bruser et al., "Automatic Detection of Atrial Fibrillation in Cardiac Vibration Signals," IEEE Journal of Biomedical Health Informatics, vol. 17, No. 1, Jan. 1, 2013. (Abstract only).
International Search Report, dated Oct. 7, 2014, from corresponding PCT application.
European Search Report 14741341.3 dated Jan. 23, 2017.
Inan et al.: "Robust ballistocardiogram acquisition for home monitoring", Physiological Measurement, Institute of Physics Publishing, Bristol, GB, vol. 30, No. 2, Feb. 1, 2009, pp. 169-185, XP020153654.

* cited by examiner

Figure 6

METHOD AND APPARATUS FOR DETERMINING INFORMATION INDICATIVE OF CARDIAC MALFUNCTIONS

FIELD OF THE INVENTION

The invention relates generally to determining information indicative of cardiac malfunctions, such as for example atrial fibrillation. More particularly, the invention relates to an apparatus and to a method for determining information indicative of cardiac malfunctions. Furthermore, the invention relates to a computer program for determining information indicative of cardiac malfunctions.

BACKGROUND

Malfunctions and abnormalities that may occur in the cardiovascular system, if not diagnosed and appropriately treated or remedied, may progressively decrease the ability of the cardiovascular system to supply, inter alia, sufficient oxygen to satisfy the coronary oxygen demand when the individual encounters stress. Currently, methods such as cardiography based on electromagnetic phenomena related to cardiac activity, echocardiography, and cardiography based on cardiovascular motion are used in the identification and assessment of various cardiac malfunctions and abnormalities. A well-known example of the cardiography based on electromagnetic phenomena related to cardiac activity is the electrocardiography "ECG", and examples of the cardiography based on cardiovascular motion are ballistocardiography "BCG" and seismocardiography "SCG". The echocardiography provides images of sections of the heart and can provide comprehensive information about the structure and function of the heart, but requires expensive equipment and specialised operating personnel. The ECG provides a fairly rapid electrical assessment of the heart, but does not provide any information relating to forces of contraction. The cardiography based on cardiovascular motion involves measurement of a signal indicative of cardiovascular motion. Earlier, the signal was obtained while an individual lay on a bed that was provided with an apparatus for measuring movements or there was a facilitating apparatus that was attached across the shin area of the legs. Currently, the signal can be obtained using small sensor elements, e.g. accelerometers, which are suitable for measuring minute movements which are representative of movements of the heart.

Figure 1A:
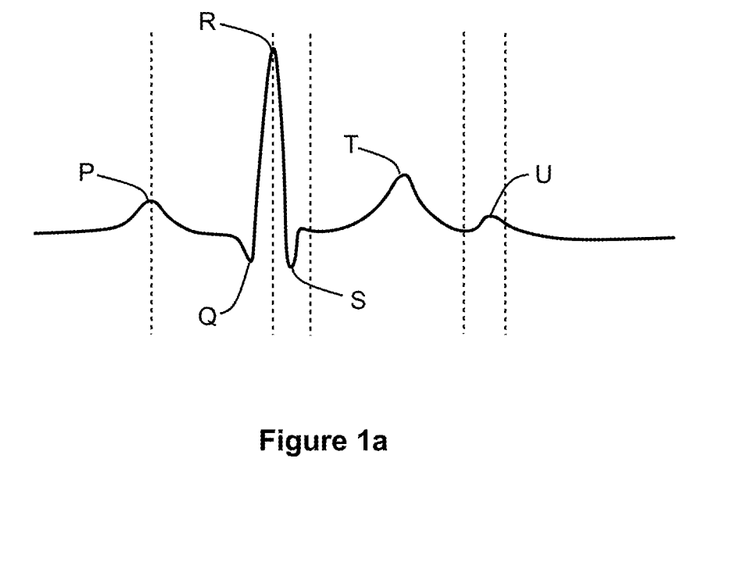
FIG. 1a illustrates an example of an ECG waveform and FIG. 1b illustrates a waveform of an exemplifying signal indicative of cardiovascular motion and measured with an accelerometer in the "head-to-foot"-direction that is typically referred to as the y-direction.
Figure 1B:
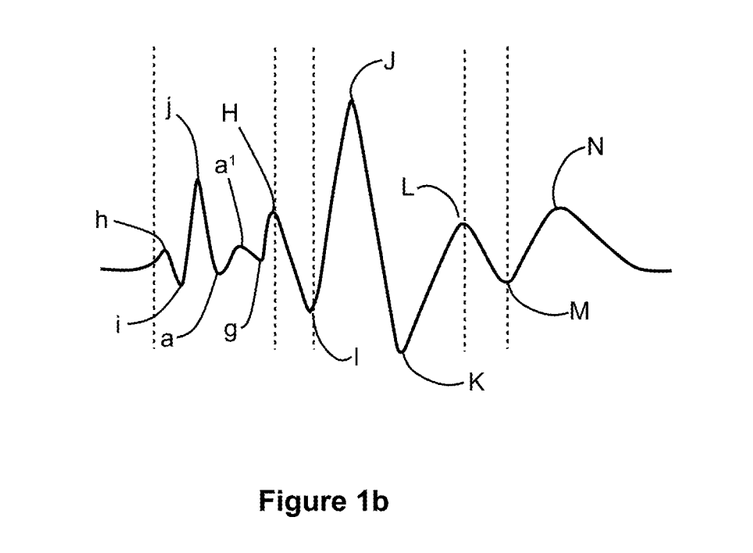

FIGS. 1a and 1b show the relationship between rhythmic electrical functions and related cardiovascular motions. FIG. 1a shows an example of an ECG waveform and FIG. 1b shows a waveform of an exemplifying signal indicative of cardiovascular motion and measured with an accelerometer in the "head-to-foot"-direction that is typically referred to as the y-direction. For the sake of illustrative purposes, a brief explanation of basic heart functions is provided below.

The heart includes four chambers. The right atrium is interconnected with the right ventricle by the tricuspid valve, and the left atrium is interconnected with the left ventricle by the mitral valve. Blood is delivered to the right atrium from the upper half of the body via the superior vena cava, and from the lower half of the body via the inferior vena cava. The tricuspid valve is opened by concurrent contraction of the right atrium myocardium and the right ventricular papillary muscles thereby allowing blood flow from the right atrium into the right ventricle. Then the tricuspid valve closes when the papillary muscles relax. When the myocardium of the right ventricle contracts, blood is forced from the right ventricle through the pulmonary valve into the pulmonary artery which delivers the blood into the lungs wherein it is oxygenated. The oxygenated blood is then delivered to the left atrium via pulmonary veins. The oxygenated blood flows from the left atrium into the left ventricle when the mitral valve is opened by concurrent contraction of the left atrium myocardium and the left ventricular papillary muscles thereby allowing blood flow from the left atrium into the left ventricle. Then the mitral valve is closed when the papillary muscles relax. The oxygenated blood is then forced out from the left ventricle through the aortic valve into the aorta which delivers the oxygenated blood to the peripheral vascular system.

Each heart-beat period involves three major stages: the atrial systole, the ventricular systole and the cardiac diastole. The atrial systole is the period of contraction of the heart muscles encompassing the right and left atria. Both atria contract concurrently with the papillary muscle contraction thereby forcing open the tricuspid valve and the mitral valve. The electrical activity, i.e. the electrical systole, which stimulates the muscle tissue of the chambers of the heart to make them contract begins in the sinoatrial node located in the right atrium. The conduction electrical depolarization continues to travel as a wave downwards, leftwards, and posteriorly through both atria depolarising each atrial muscle cell in turn. This propagation of charge can be seen as the P-wave on the ECG waveform shown in FIG. 1a. This is closely followed by mechanical contraction of the atria that is detected as an impact which corresponds to the h-peak of the waveform shown in FIG. 1b and to a recoil which corresponds to the i-valley of the waveform shown in FIG. 1b. When the right and left atria begin to contract, there is a high velocity flow of blood into the right and left ventricles, which is represented by the j-peak on the waveform shown in FIG. 1b. The continuing atrial contraction, when the tricuspid valve begins to close, causes an additional lower velocity flow of blood into the right and left ventricles. The additional flow of blood is called the "atrial kick", which corresponds to the "a-a$^1$"-wave complex in the waveform shown in FIG. 1b. After the atria are emptied, the tricuspid and mitral valves close thereby giving rise to the downward g-wave on the waveform shown in FIG. 1b. The ventricular systole is the contraction of the muscles of the left and right ventricles, and is caused by the electrical depolarization of the ventricular myocardia giving rise to the "Q-R-S"-wave complex in the ECG waveform shown in FIG. 1a. The downward Q-wave is caused by the downward flow of depolarisation through the septum along a specialized group of cells called "the bundle of His". The R-peak is caused by depolarization of the ventricular muscle tissue, and the S-wave is produced by depolarization of the heart tissue between the atria and ventricles. As the depolarization travels down the septum and throughout the ventricular myocardia, the atria and sinoatrial node start to polarise. The closing of the tricuspid and mitral valves mark the beginning of ventricular systole and cause the first part of the "lub-dub" sound made by the heart as it beats. This sound is typically known as the "first heart tone". When the electrical depolarization of the ventricular myocardia peaks, the atrioventricular "AV" septum separating the right and left ventricles contracts causing an impact, which corresponds to the H-peak on the waveform shown in FIG. 1b, and a recoil which corresponds to the I-valley on the waveform shown in FIG. 1b. The ventricular contraction forces the blood from the right ventricle into the pulmonary artery through the pulmonary valve, and from the left ventricle into the aorta through the aortic valve under very high velocity thereby causing the J-peak on the waveform shown in FIG. 1b. The deceleration of blood flow from the left ventricle into the aorta causes the downward K-wave on the waveform shown in FIG. 1b. When the left ventricle empties, its pressure falls below the pressure in the aorta and the aortic valve closes. Similarly, when the pressure in the right ventricle falls below the pressure in the pulmonary artery, the pulmonary valve closes. The second part of the "lub-dub" sound, which is typically known as the "second heart tone", is caused by the closure of the pulmonary and aortic valves at the end of ventricular systole thereby causing the upward L-wave on the waveform shown in FIG. 1b. Concurrently with the closing of the pulmonary and aortic valves, the atrioventricular "AV" septum relaxes and moves upward, and the ventricular myocardia is re-polarized giving rise to the T-wave on the ECG waveform shown in FIG. 1a. The cardiac diastole, which includes the atrial diastole and the ventricular diastole, is the period when the heart relaxes after contraction and prepares for being refilled with circulating blood. Atrial diastole is when the right and left atria are relaxing, and the ventricular diastole is when the right and left ventricles are relaxing. During the period of the atrial diastole, the right atrium is re-filled by deoxygenated blood while the left atrium is re-filled with oxygenated blood. Re-filling of the atria causes the downward M-wave on the waveform shown in FIG. 1b early in the diastole which coincides with repolarization of the bundle of His cells, which is shown as the U-wave in the ECG waveform. When the right and left atria are filled to their maximum capacities, the reflux of blood against the tricuspid valve and mitral valve cause the upward N-wave on the waveform shown in FIG. 1b.

Analysis of waveforms indicative of cardiovascular motion and/or waveforms indicative of electromagnetic phenomena related to cardiac activity is typically performed visually by qualified diagnosticians in order to distinguish abnormal cardiovascular function from normal cases. In many cases, however, it may be challenging to find out certain cardiac malfunctions, such as for example atrial fibrillation, by visual analysis. Thus, a need exists for methods and apparatuses for determining information indicative of cardiac malfunctions.

Publication U.S. Pat. No. 7,846,106 describes a method for detecting atrial fibrillation in a patient by monitoring the blood oxygen saturation level over a period of time. The method comprises producing a plethysmographic waveform from the monitored blood oxygen saturation level, analysing the plethysmographic waveform and detected intervals, and determining whether the patient is in atrial fibrillation.

SUMMARY

The following presents a simplified summary in order to provide a basic understanding of some aspects of various invention embodiments. The summary is not an extensive overview of the invention. It is neither intended to identify key or critical elements of the invention nor to delineate the scope of the invention. The following summary merely presents some concepts of the invention in a simplified form as a prelude to a more detailed description of exemplifying embodiments of the invention.

In accordance with the invention, there is provided a new method for determining information indicative of cardiac malfunctions, e.g. atrial fibrillation. The method according to the invention comprises:

determining, based on a signal indicative of cardiovascular motion, a correlation between amplitudes of heartbeats and quantities indicative of heartbeat rates prior to the heartbeats to detect whether the time-trend of the signal manifests an indicative phenomenon where the amplitude of a first heartbeat is greater than the amplitude of a second heartbeat and the heartbeat rate is greater prior to the first heartbeat than prior to the second heartbeat, and producing an indicator of cardiac malfunction, e.g. atrial fibrillation, in response to detection of the indicative phenomenon.

The amplitudes of the heartbeats can be, for example but not necessarily, the heights of the aortic valve opening "AO"-peaks on a waveform indicative of cardiovascular motion measured in the "through chest"-direction that is typically referred to as the z-direction, and the heartbeat rates prior to the heartbeats whose amplitudes are considered can be indicated with the aid of temporal lengths of heartbeat periods preceding these heartbeats. The heartbeat periods can be represented, for example but not necessarily, by time periods between successive AO-peaks. For another non-limiting example, the heartbeat periods can be represented by R-R intervals extracted from an ECG-signal indicative of the electromagnetic phenomena related to cardiac activity. For a further non-limiting example, it is also possible that the amplitudes of the heartbeats are the heights of the J-peaks on a waveform indicative of cardiovascular motion measured with an accelerometer in the "head-to-foot"-direction that is typically referred to as the y-direction.

The above-mentioned indicative phenomenon where greater heartbeat amplitude can be preceded by a shorter heartbeat period, i.e. a higher temporary heartbeat rate, and smaller heartbeat amplitude can be preceded by a longer heartbeat period, i.e. a lower temporary heartbeat rate, can be used as the indicator of cardiac malfunction. For example, in light of empirical data, occurrence of the indicative phenomenon means an increased probability of atrial fibrillation. Furthermore, in light of empirical data, the indicative phenomenon can be used, for example, for finding out whether there is a physiological state where atrial fibrillation takes place or a physiological state where atrial extra systoles take place.

The indicative phenomenon can be detected, for example, by searching from an appropriate waveform whether there are greater heartbeat amplitudes preceded by shorter heartbeat periods and smaller heartbeat amplitudes preceded by longer heartbeat periods, or by determining correlation between amplitudes of heartbeats and quantities indicative of the heartbeat rates prior to these heartbeats. For example, a negative correlation between the amplitudes of the heartbeats and the temporal lengths of the heartbeat periods preceding these heartbeats expresses the presence of the indicative phenomenon. Correspondingly, a positive correlation between the amplitudes of the heartbeats and heartbeat rates on the heartbeat periods preceding these heartbeats expresses the presence of the indicative phenomenon.

In accordance with the invention, there is provided also a new apparatus for determining information indicative of cardiac malfunctions. The apparatus according to the invention comprises:

a signal interface for receiving a signal indicative of cardiovascular motion, and a processing device coupled to the signal interface and configured to:

a) determine, based on the signal indicative of cardiovascular motion, a correlation between amplitudes of heartbeats and quantities indicative of heartbeat rates prior to the heartbeats to detect whether the time-trend of the signal manifests an indicative phenomenon where the amplitude of a first heartbeat is greater than the amplitude of a second heartbeat and the heartbeat rate is greater prior to the first heartbeat than prior to the second heartbeat, and b) produce an indicator of cardiac malfunction, e.g. atrial fibrillation, in response to detection of the indicative phenomenon.

The apparatus may further comprise a sensor element for measuring the signal indicative of cardiovascular motion. The sensor element may comprise, for example, an accelerometer, a piezo-electronic sensor, or any other element suitable for measuring force, acceleration, displacement, or any other quantity related to and indicative of cardiovascular motion. It is also possible that the signal interface is capable of receiving the signal from an external device comprising an appropriate sensor element, i.e. it is emphasized that the apparatus does not necessarily comprise means for measuring the signal indicative of cardiovascular motion.

In accordance with the invention, there is provided also a new computer program for determining information indicative of cardiac malfunctions. The computer program comprises computer executable instructions for controlling a programmable processor to:

determine, based on a signal indicative of cardiovascular motion, a correlation between amplitudes of heartbeats and quantities indicative of heartbeat rates prior to the heartbeats to detect whether the time-trend of the signal manifests an indicative phenomenon where the amplitude of a first heartbeat is greater than the amplitude of a second heartbeat and the heartbeat rate is greater prior to the first heartbeat than prior to the second heartbeat, and produce an indicator of cardiac malfunction, e.g. atrial fibrillation, in response to detection of the indicative phenomenon.

In accordance with the invention, there is provided also a new computer program product. The computer program product comprises a non-volatile computer readable medium, e.g. a compact disc "CD", encoded with a computer program according to the invention.

A number of non-limiting and exemplifying embodiments of the invention are described in accompanied dependent claims.

Various exemplifying embodiments of the invention both as to constructions and to methods of operation, together with additional objects and advantages thereof, will be best understood from the following description of specific exemplifying embodiments when read in connection with the accompanying drawings.

The verbs "to comprise" and "to include" are used in this document as open limitations that neither exclude nor require the existence of also un-recited features. The features recited in depending claims are mutually freely combinable unless otherwise explicitly stated. Furthermore, it is to be understood that the use of "a" or "an", i.e. a singular form, throughout this document does not exclude a plurality.

BRIEF DESCRIPTION OF FIGURES

The exemplifying embodiments of the invention and their advantages are explained in greater detail below with reference to the accompanying drawings, in which:

FIGS. 1a and 1b have already been explained when describing the background of the invention.

DESCRIPTION OF EXEMPLIFYING EMBODIMENTS

Figure 2:
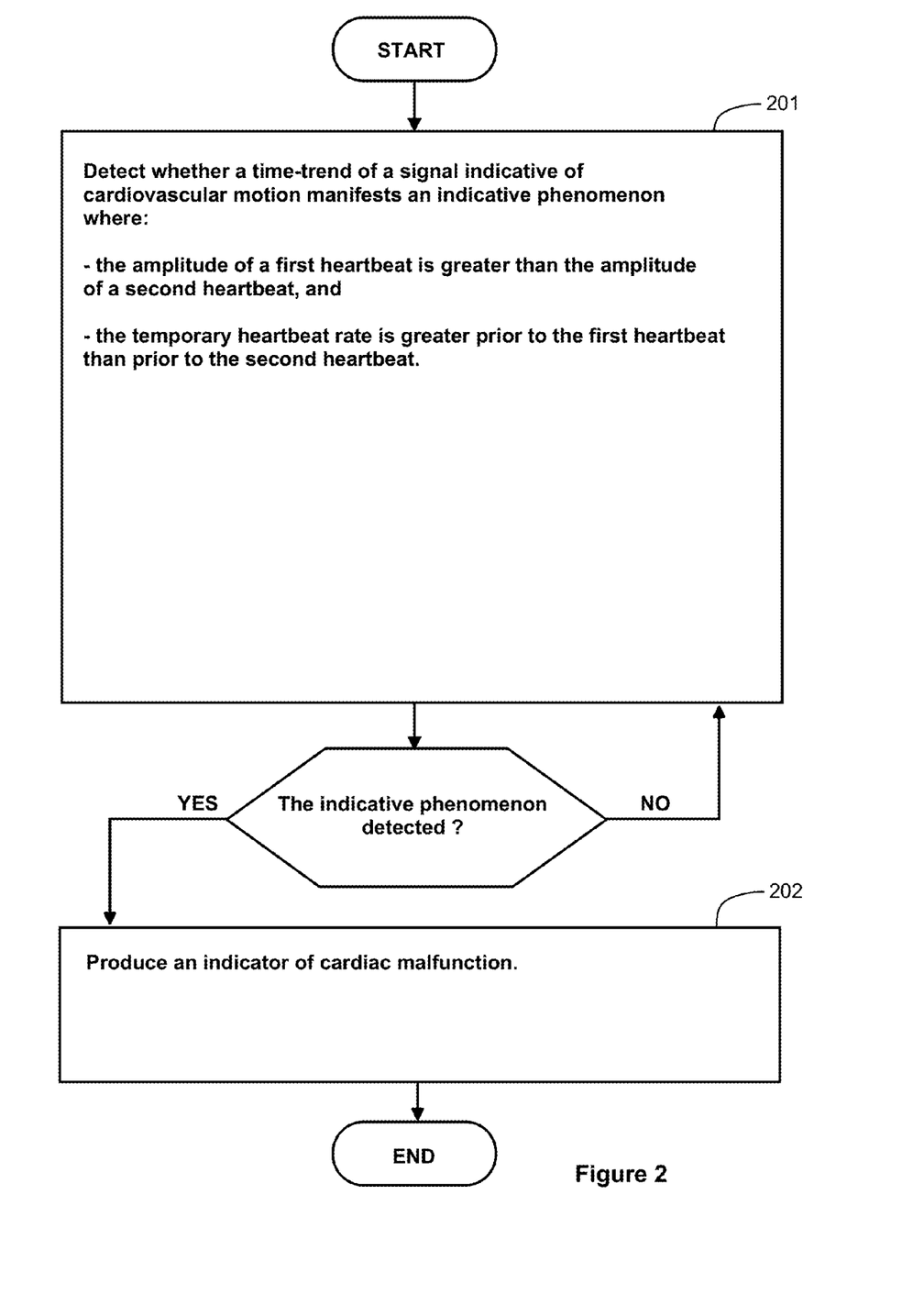
FIG. 2 illustrates a flow chart of a method according to an exemplifying embodiment of the invention for determining information indicative of cardiac malfunctions and abnormalities.

FIG. 2 illustrates a flow chart of a method according to an exemplifying embodiment of the invention for determining information indicative of cardiac malfunctions, e.g. atrial fibrillation. The method comprises, in a phase 201, detecting whether the time-trend of a first signal indicative of cardiovascular motion manifests an indicative phenomenon where the amplitude of a first heartbeat is greater than the amplitude of a second heartbeat and the temporary heartbeat rate is greater prior to the first heartbeat than prior to the second heartbeat. The method further comprises, in a phase 202, producing an indicator of cardiac malfunction in response to detection of the indicative phenomenon. For example the temporal length of a heartbeat period preceding each heartbeat, whose amplitude is to be considered, can be used as a quantity indicative of the heartbeat rate prevailing prior to this heartbeat. In some cases, it is also possible to detect the quantity indicative of the heartbeat rate prevailing prior to the heartbeat under consideration from two or more successive heartbeat periods preceding the heartbeat.

Figure 3A:
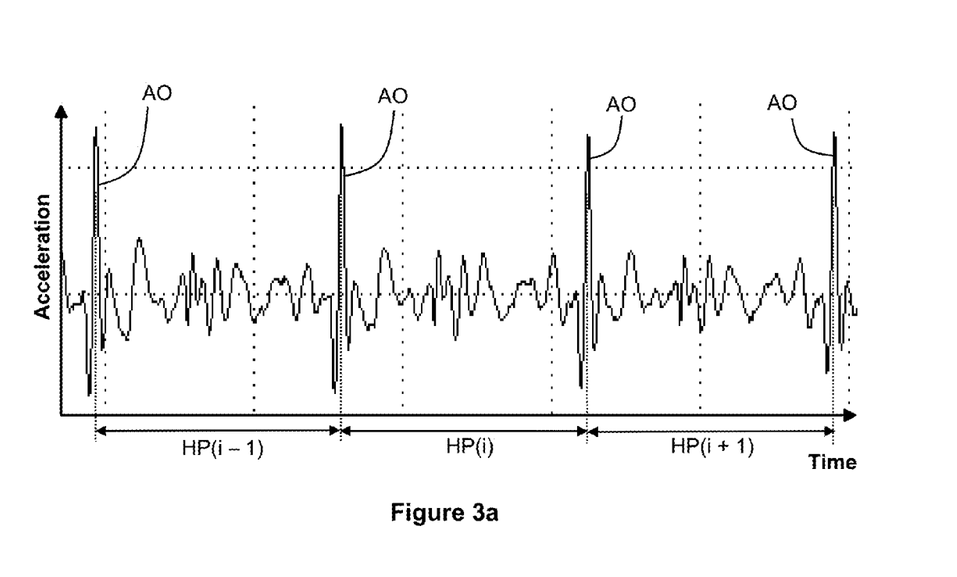
FIG. 3a illustrates a waveform of an exemplifying signal indicative of cardiovascular motion over several heart-beat periods in a normal case when an individual under consideration is at rest and FIG. 3b illustrates an exemplifying ECG-waveform measured from the same individual at the same time, the waveform shown in FIG. 3a has been measured with an accelerometer in the "through chest"-direction that is typically referred to as the z-direction.
Figure 3B:
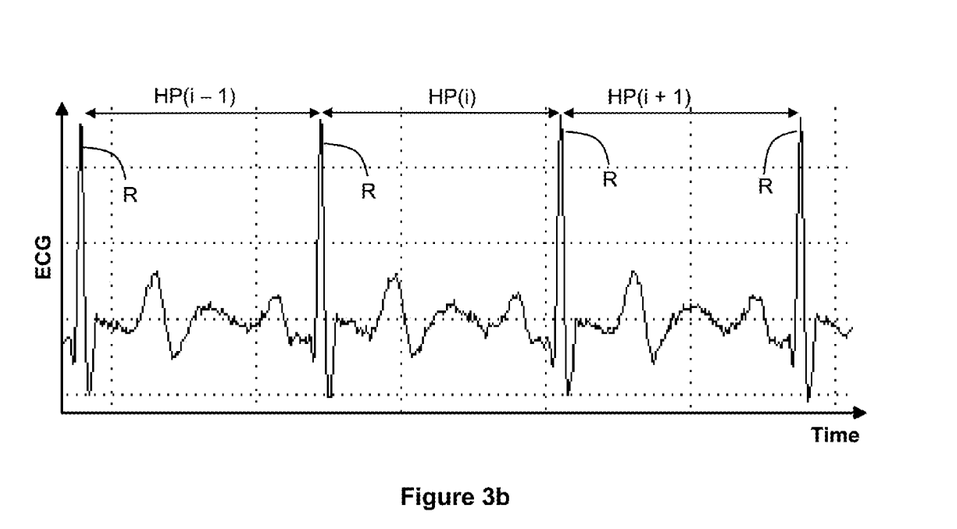
Figure 6:
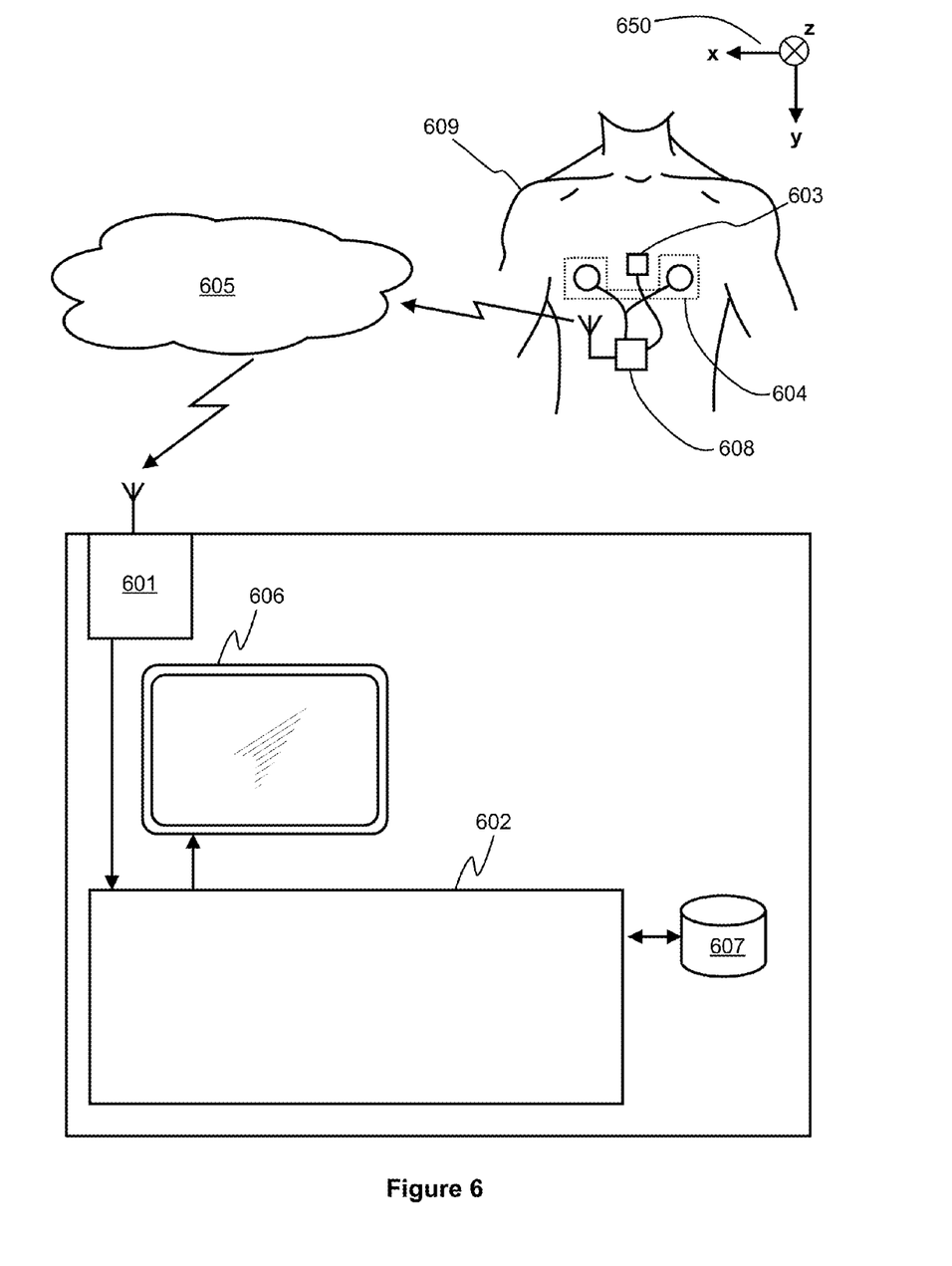
FIG. 6 shows a schematic illustration of an apparatus according to an exemplifying embodiment of the invention for determining information indicative of cardiac malfunctions and abnormalities.

FIG. 3a illustrates a waveform of an exemplifying signal indicative of cardiovascular motion over several heart-beat periods in a normal case when an individual under consideration is at rest. FIG. 3b illustrates a waveform of an exemplifying signal indicative of electromagnetic phenomena related to cardiac activity. The waveforms shown in FIGS. 3a and 3b correspond to each other so that they have been measured simultaneously from a same individual. The waveform shown in FIG. 3a has been measured with an accelerometer in the "through chest"-direction that is typically referred to as the z-direction. A coordinate system 650 shown in FIG. 6 illustrates the z-direction. The waveform shown in FIG. 3b is an ECG waveform that has been measured with the aid of electrodes attached to the individual's chest.

Figure 4A:
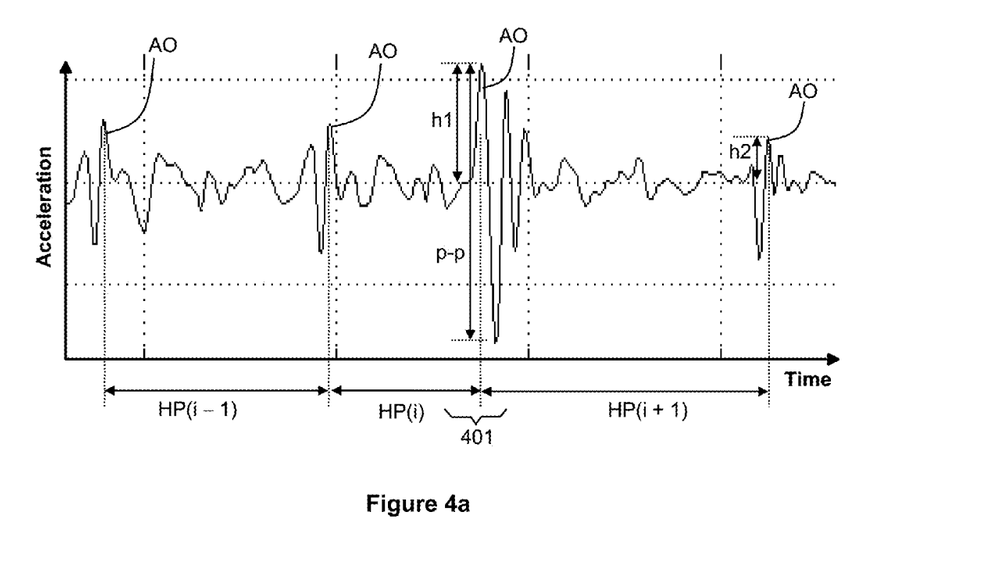
FIG. 4a illustrates a waveform of an exemplifying signal indicative of cardiovascular motion over several heart-beat periods in a case of atrial fibrillation when an individual under consideration is at rest.
Figure 4B:
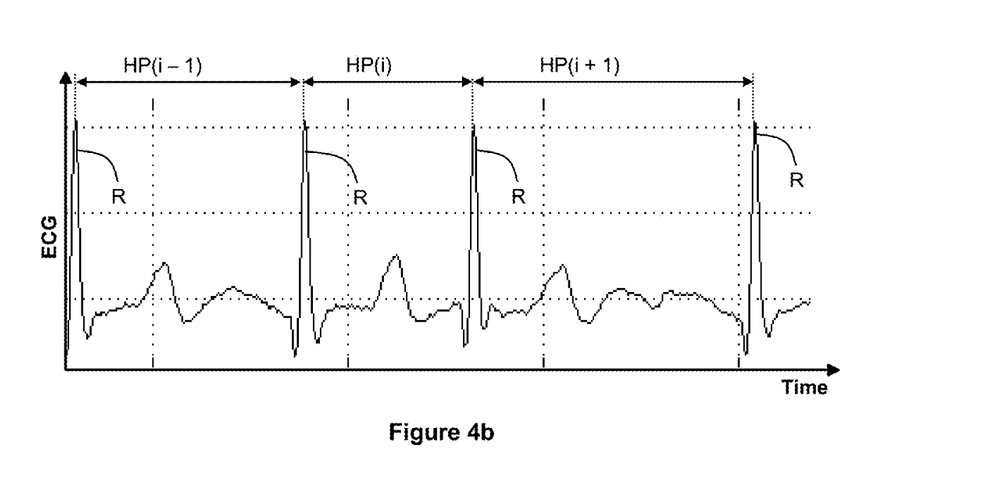
FIG. 4b illustrates an exemplifying ECG waveform measured from the same individual at the same time.

FIG. 4a illustrates a waveform of an exemplifying signal indicative of cardiovascular motion over several heart-beat periods in an exemplifying case of atrial fibrillation when an individual under consideration is at rest. FIG. 4b illustrates a waveform of an exemplifying signal indicative of electromagnetic phenomena related to cardiac activity. The waveforms shown in FIGS. 4a and 4b correspond to each other so that they have been measured simultaneously from a same individual. The waveforms shown in FIGS. 4a and 4b have been measured with the same methods as the waveforms shown in FIGS. 3a and 3b, respectively.

As can be seen from FIGS. 3a and 4a, the variation of the amplitude between different heartbeats, i.e. the amplitude variation, is significantly larger in the case of atrial fibrillation than in the normal case. The amplitudes of the heartbeats can be quantified, for example, with heights of the AO-peaks caused by opening of the aortic valve. Furthermore, it is also possible to express the amplitudes with maximum peak-to-peak values within time windows each involving one of the AO-peaks or with root-mean-square "RMS" values computed over suitable time windows each involving one of the AO-peaks. In FIG. 4a, the heights of two of the AO-peaks are denoted with "h1" and "h2", and the maximum peak-to-peak value within a time window 401 involving one of the AO-peaks is denoted with "p-p". An extremum that represents the height of a single AO-peak or that is needed for computing a peak-to-peak value can be taken as a single point by searching a local maximum or minimum. Alternatively, the extremum can be obtained so that many samples are taken first from a time-window covering the wave pattern under consideration and then an estimate of the extremum is computed as a mathematical function, e.g. an arithmetic mean, of the samples in order to mitigate the effect of noise. The time window can be e.g. 100 ms, and the number of samples within the time window can be e.g. ten or more. The method based on the time-window is an example of digital filtering. Generally, there are numerous digital and analogue signal processing methods that can be used for mitigating the effect of noise in signals indicative of cardiovascular motion and in signals indicative of electromagnetic phenomena related to cardiac activity.

Furthermore, as can be seen from FIGS. 3a, 3b, 4a and 4b, the variation of the temporal lengths of the heartbeat periods, i.e. the time variation, is is significantly larger in the case of the atrial fibrillation than in the normal case. In FIGS. 3a, 3b, 4a and 4b, three successive heartbeat periods are denoted with HP(i-1), HP(i), and HP(i+1) where i is an integer. In FIGS. 3a and 4a, the heartbeat periods are defined to be time periods between successive AO-peaks, and in FIGS. 3b and 4b the heartbeat periods are defined to be time periods between successive R-peaks, i.e. R-R intervals. In cases where the heartbeat periods are defined as time periods between successive AO-peaks, the waveform indicative of cardiovascular motion is advantageously low-pass filtered prior to searching the temporal locations of the AO-peaks because the low-pass filtering facilitates the detection of the temporal locations of the AO-peaks. The upper limit frequency of the low-pass filtering can be, for example but not necessarily, 30 Hz.

In a method according to an exemplifying embodiment of the invention, the presence of the phenomenon indicative of cardiac malfunctions, e.g. atrial fibrillation, is detected by searching from the waveform indicative of cardiovascular motion whether there are greater heartbeat amplitudes preceded by shorter heartbeat periods and smaller heartbeat amplitudes preceded by longer heartbeat periods. As can be seen, the waveform corresponding to the normal case and shown in FIG. 3a does not comprise heartbeat amplitudes and periods that would clearly have the above-mentioned properties whereas the waveform corresponding to the case of atrial fibrillation and shown in FIG. 4a manifests the indicative phenomenon where, for example, the amplitude h1 of a first heartbeat is greater than the amplitude h2 of a second heartbeat and the heartbeat period HP(i) preceding the first heartbeat is shorter than the heartbeat period HP(i+1) preceding the second heartbeat.

In a method according to another exemplifying embodiment of the invention, the presence of the phenomenon indicative of cardiac malfunctions, e.g. atrial fibrillation, is detected by determining correlation between the amplitudes of the heartbeats and quantities indicative of the temporary heartbeat rates prior to the heartbeats. The correlation can be, for example, the correlation between the amplitudes of the heartbeats and the temporal lengths of the heartbeat periods preceding these heartbeats. In this case, a negative correlation indicates the presence of the indicative phenomenon. For another example, the correlation can be the correlation between the amplitudes of the heartbeats and the heartbeat rates on the heartbeat periods preceding the heartbeats, i.e. the inverse values of the temporal lengths of the heartbeat periods preceding the heartbeats. In this case, a positive correlation indicates the presence of the indicative phenomenon. The temporal lengths of the heartbeat periods can be, for example, the temporal lengths of the R-R-intervals or the AO-AO intervals.

The degree of the correlation between the amplitudes of the heartbeats and the quantities indicative of the heartbeat rates prior to the heartbeats can be expressed with the aid of a mathematical correlation coefficient C that can be computed, for example, according to the following equations:

$$C = \frac{\sum_{i=1}^{N}[(A(i) - \mu_A) \times (Q(i) - \mu_Q)]}{N-1}, \quad (1)$$

where N is the number of heartbeats under consideration, A(i) is the amplitude of the $i^{th}$ heartbeat, Q(i) is the quantity indicative of the heartbeat rate prior to the $i^{th}$ heartbeat e.g. the temporal length of the heartbeat period preceding the $i^{th}$ heartbeat, and $$\mu_A = \frac{\sum_{i=1}^{N} A(i)}{N}, \mu_Q = \frac{\sum_{i=1}^{N} Q(i)}{N}. \quad (2)$$

The above-presented correlation coefficient C can be used as the indicator of cardiac malfunction. A method according to an exemplifying embodiment of the invention comprises comparing the correlation coefficient C to a threshold and producing a signal expressing atrial fibrillation or some other cardiac malfunction and/or abnormality in accordance with the result of the comparison. A suitable value for the threshold can be determined on the basis of empirical data gathered from a group of patients and/or other persons. The threshold is not necessary a constant but the threshold can be changing according to the individual under consideration, according to time, and/or according to some other factors. It is also possible to construct a series of thresholds where each threshold represents a specific probability of atrial fibrillation or some other cardiac malfunction and/or abnormality.

Figure 5A:
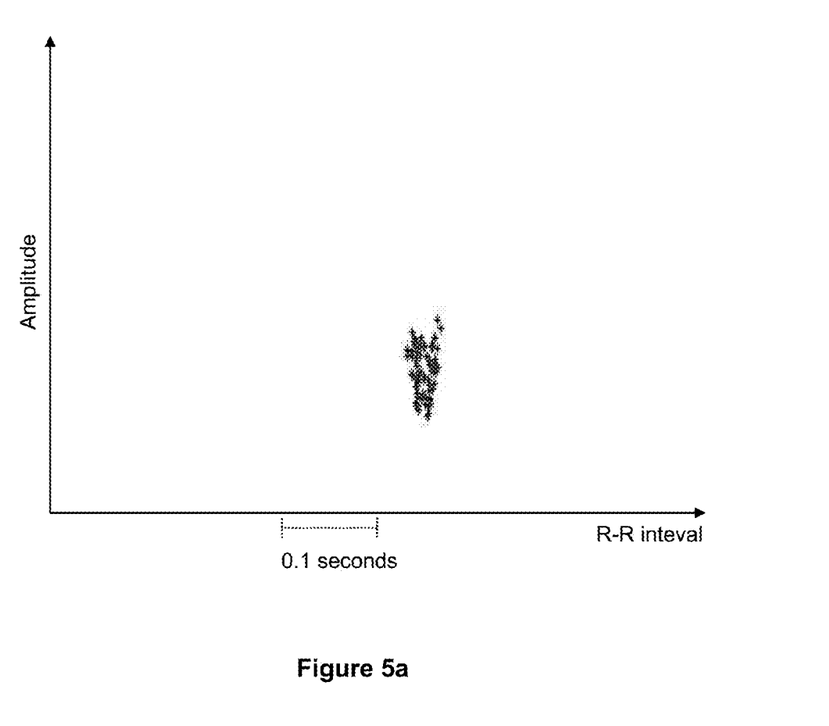
FIGS. 5a, 5b and 5c present heartbeats as points in a two-dimensional coordinate system where the coordinates of each point are the amplitude of the heartbeat and the R-R interval preceding the heartbeat, wherein FIG. 5a corresponds to a normal case when an individual under consideration is at rest, FIG. 5b corresponds to an exemplifying case of atrial fibrillation when an individual under consideration is at rest, and FIG. 5c corresponds to another exemplifying case of atrial fibrillation when an individual under consideration is at rest.
Figure 5B:
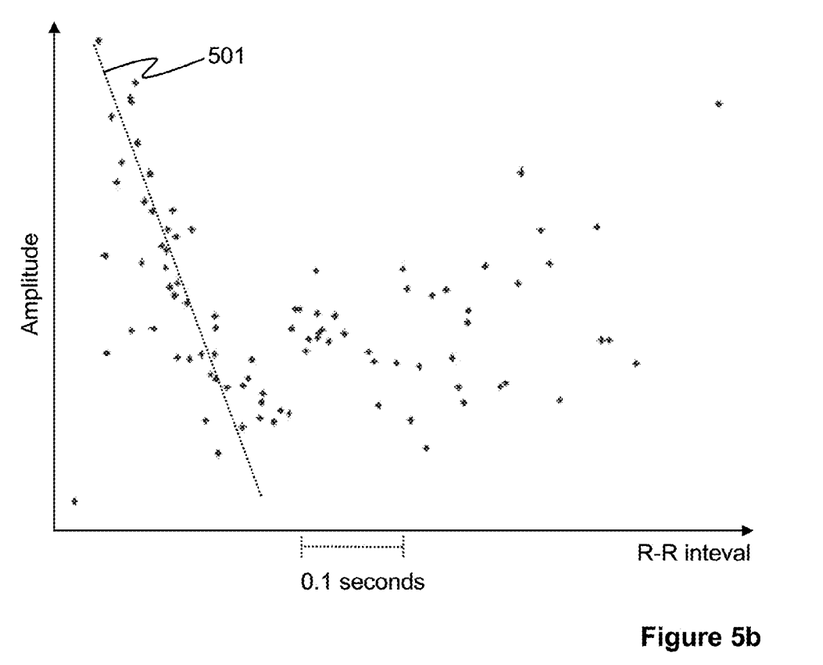
Figure 5C:
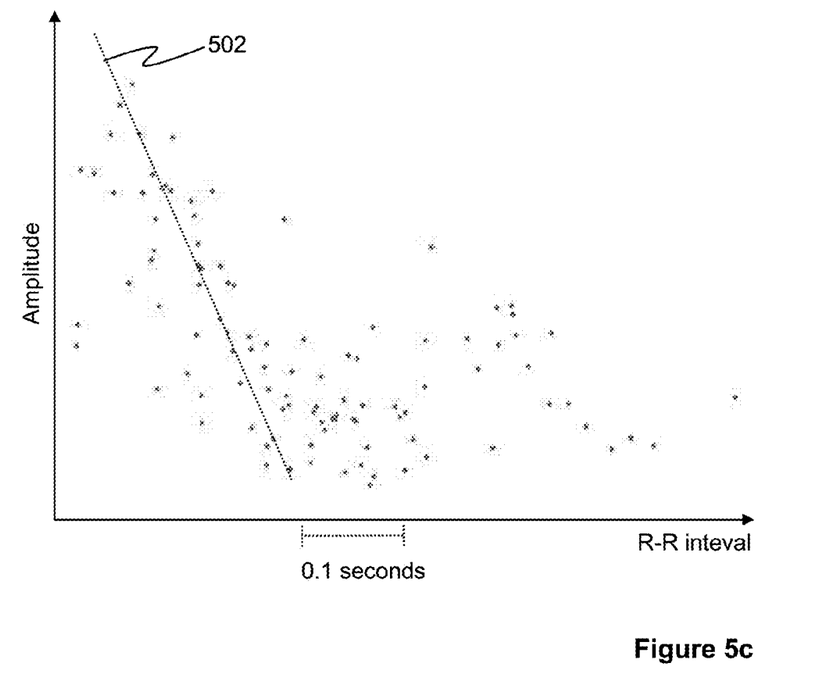

FIGS. 5a, 5b and 5c present heartbeats as points in a two-dimensional coordinate system where the coordinates of each point are the amplitude of the heartbeat and the R-R interval preceding the heartbeat. FIG. 5a corresponds to a normal case when an individual under consideration is at rest, FIG. 5b corresponds to an exemplifying case of atrial fibrillation when an individual under consideration is at rest, and FIG. 5c corresponds to another exemplifying case of atrial fibrillation when an individual under consideration is at rest.

In the normal case illustrated by FIG. 5a, the variation of the R-R interval, i.e. the time variation, is small and no correlation between the R-R intervals and the amplitudes is visible. In the exemplifying case of atrial fibrillation illustrated in FIG. 5b, there is a significantly stronger time variation and the lower part of the range of variation of the R-R interval manifests a behaviour where the amplitude tends to increase when the R-R interval decreases, i.e. in this part of the range of variation of the R-R interval, there is a negative correlation between the amplitudes and the R-R intervals. In FIG. 5b, the negative correlation is illustrated with a line 501 that has a negative angular coefficient. The same phenomenon is shown also in FIG. 5c where a line 502 illustrates the negative correlation.

A method according to an exemplifying embodiment of the invention comprises a two-phase procedure so that a measure for the time variation indicative of the variation of the temporal lengths of the heartbeat periods is determined first and, if the time variation exceeds a threshold, it is detected whether the time-trend of the signal indicative of cardiovascular motion manifests the phenomenon indicative of cardiac malfunctions, e.g. atrial fibrillation.

The strength of the above-mentioned time variation can be expressed with the aid of a mathematical variation-quantity V that can be computed, for example, according to the following equations:

$$V = \frac{\sqrt{\frac{\sum_{i=1}^{M} (TL(i) - \mu_T)^2}{M-1}}}{\mu_T} \times 100\% \quad (3)$$

where M is the number of the heartbeat periods under consideration and TL(i) is the temporal length of the $i^{th}$ heartbeat period, and $$\mu_T = \frac{\sum_{i=1}^{M} TL(i)}{M}. \quad (4)$$

Figure 4C:
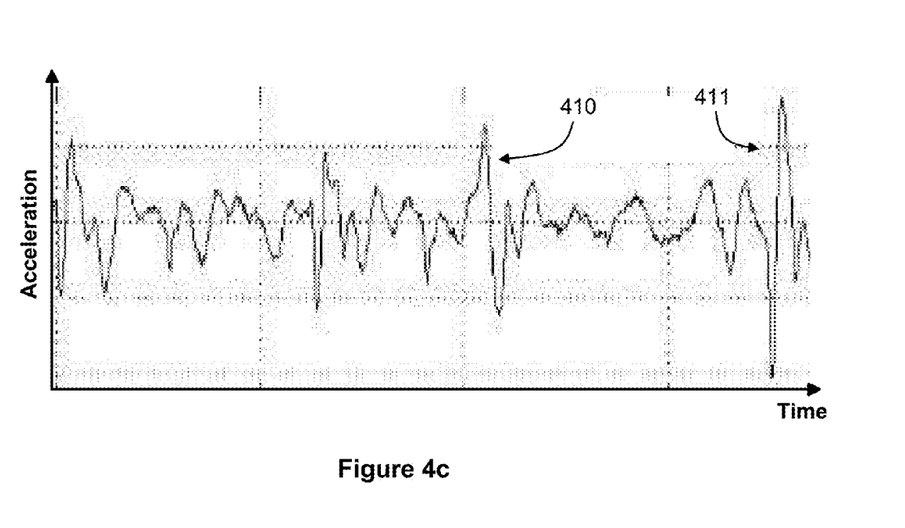
FIG. 4c illustrates a waveform of an exemplifying signal indicative of cardiovascular motion in an exemplifying case where an atrial extra systole occurs, the waveforms shown in FIGS. 4a and 4c have been measured with an accelerometer in the "through chest"-direction that is typically referred to as the z-direction.

In light of empirical data, the variation-quantity V can be about 10% during atrial fibrillation and about 1-2% in a normal case. The detection of the indicative phenomenon, e.g. the negative correlation between the amplitudes and the R-R intervals, makes it easier to find out whether there is a physiological state where atrial fibrillation takes place or a physiological state where there are atrial extra systoles which also cause time variation. FIG. 4c shows a waveform of an exemplifying signal indicative of cardiovascular motion in an exemplifying case where a heartbeat 410 that is an atrial extra systole occurs. As can be seen from FIG. 4c, there is significant time variation but no significant negative correlation between the amplitudes and the temporal lengths of the heart beat periods. Actually, the amplitudes of the heartbeats 410 and 411 and the temporal lengths of the heart beat periods preceding these heartbeats show positive correlation between the amplitudes and the temporal lengths of the heart beat periods.

A method according to an exemplifying embodiment of the invention comprises optionally measuring the signal indicative of cardiovascular motion with a sensor element from an individual's body. A method according to another exemplifying embodiment of the invention comprises reading this signal from a memory, in which case the signal has been measured earlier and recorded to the memory. A method according to an exemplifying embodiment of the invention comprises receiving the signal from an external data transfer system. Hence, the measuring is not an essential and necessary step of methods according to embodiments of the invention.

A computer program according to an exemplifying embodiment of the invention comprises computer executable instructions for controlling a programmable processor to carry out a method according to one or more of the above-described exemplifying embodiments of the invention.

A computer program according to an exemplifying embodiment of the invention comprises software modules for determining information indicative of cardiac malfunctions. The software modules comprise computer executable instructions for controlling a programmable processor to:
  detect whether the time-trend of a signal indicative of cardiovascular motion manifests an indicative phenomenon where the amplitude of a first heartbeat is greater than the amplitude of a second heartbeat and the heartbeat rate is greater prior to the first heartbeat than prior to the second heartbeat, and
  produce an indicator of cardiac malfunction, e.g. atrial fibrillation, in response to detection of the indicative phenomenon.

The software modules can be e.g. subroutines or functions implemented with a suitable programming language and with a compiler suitable for the programming language and the programmable processor.

A computer program product according to an exemplifying embodiment of the invention comprises a computer readable medium, e.g. a compact disc "CD", encoded with a computer program according to an embodiment of invention.

A signal according to an exemplifying embodiment of the invention is encoded to carry information defining a computer program according to an embodiment of invention.

FIG. 6 shows a schematic illustration of an apparatus according to an exemplifying embodiment of the invention for determining information indicative of cardiac malfunctions. The apparatus comprises a signal interface 601 for receiving a first signal indicative of cardiovascular motion. The apparatus comprises a processing device 602 coupled to the signal interface. The processing device is configured to detect whether the time-trend of the first signal manifests an indicative phenomenon where the amplitude of a first heartbeat is greater than the amplitude of a second heartbeat and the heartbeat rate, beats per second, is greater prior to the first heartbeat than prior to the second heartbeat, and produce an indicator of cardiac malfunction, e.g. atrial fibrillation, in response to detection of the indicative phenomenon.

In an apparatus according to an exemplifying embodiment of the invention, the processing device 602 is configured to use the temporal length of the heartbeat period preceding the first heartbeat as a quantity indicative of the heartbeat rate prior to the first heartbeat, and the temporal length of the heartbeat period preceding the second heartbeat as a quantity indicative of the heartbeat rate prior to the second heartbeat.

In an apparatus according to an exemplifying embodiment of the invention, the processing device 602 is configured to determine correlation between the amplitudes of the heartbeats and quantities indicative of the heartbeat rates prior to the heartbeats so as to detect the indicative phenomenon.

In an apparatus according to an exemplifying embodiment of the invention, the processing device 602 is configured to determine the correlation between the amplitudes of the heartbeats and the temporal lengths of the heartbeat periods preceding the heartbeats. In this case, a negative correlation indicates the presence of the indicative phenomenon.

In an apparatus according to another exemplifying embodiment of the invention, the processing device 602 is configured to determine the correlation between the amplitudes of the heartbeats and the heartbeat rates on the heartbeat periods preceding the heartbeats. In this case, a positive correlation indicates the presence of the indicative phenomenon.

In an apparatus according to an exemplifying embodiment of the invention, the processing device 602 is configured to compute a correlation coefficient C indicative of the degree of the correlation between the amplitudes of the heartbeats and the quantities indicative of the heartbeat rates prior to the heartbeats according to the following equation:

$$C = E\{(A-\mu_A) \times (Q-\mu_Q)\},$$

where E is the expected value operator, A represents the amplitudes of the heartbeats, $\mu_A$ is the mean of the amplitudes, Q represents the quantities indicative of the heartbeat rates, and $\mu_Q$ is the mean of the quantities indicative of the heartbeat rates.

Furthermore, the processing device 602 can be configured to compare the computed correlation coefficient C with one or more thresholds and to produce a signal expressing cardiac malfunction in response to the situation in which the result of the comparison indicates the presence of cardiac malfunction. The signal can be, for example, a message shown on a display screen 606. The one or more thresholds are preferably adjustable parameters that can be supplied to the apparatus via its user interface.

In an apparatus according to an exemplifying embodiment of the invention, the processing device 602 is configured to extract or produce, from or on the basis of the first signal indicative of cardiovascular motion, one of the following which represent the amplitudes of the heartbeats: heights of AO-peaks caused by opening of the aortic valve, maximum peak-to-peak values within time windows each involving one of the AO-peaks, or root-mean-square "RMS" values computed over time windows each involving one of the AO-peaks.

In an apparatus according to an exemplifying embodiment of the invention, the processing device 602 is configured to extract, from the first signal indicative of cardiovascular motion, time periods between successive AO-peaks. In this case, the temporal lengths of the time periods between successive AO-peaks or the inverse values of the temporal lengths can be used as the quantities indicative of the heartbeat rates prior to the heartbeats. The processing device 602 is advantageously configured to low-pass filter the first signal prior to searching the temporal locations of the AO-peaks because the low-pass filtering facilitates the detection of the temporal locations of the AO-peaks. The upper limit frequency of the low-pass filtering can be, for example but not necessarily, 30 Hz.

In an apparatus according to an exemplifying embodiment of the invention, the signal interface 601 is configured to receive a second signal indicative of electromagnetic phenomena related to cardiac activity, and the processing device 602 is configured to extract, from the second signal, time periods between successive R-peaks that are caused by depolarization of the ventricular muscle tissue. In this case, the temporal lengths of the time periods between the successive R-peaks or the inverse values of the temporal lengths can be used as the quantities indicative of the temporary heartbeat rates prior to the heartbeats.

In an apparatus according to an exemplifying embodiment of the invention, the processing device 602 is configured to first determine time variation indicative of variation of the temporal lengths of the heartbeat periods and then, if the detected time variation exceeds a threshold, detect whether the time-trend of the first signal indicative of cardiovascular motion manifests the indicative phenomenon.

In an apparatus according to an exemplifying embodiment of the invention, the processing device 602 is configured to compute a variation-quantity V indicative of the time variation according to the following equation:

$$V = \frac{\sqrt{E\{(TL-\mu_T)^2\}}}{\mu_T},$$

where E is the expected value operator, TL represents the temporal lengths of the heartbeat periods, and $\mu_T$ is the mean of the temporal lengths of the heartbeat periods.

An apparatus according to an exemplifying embodiment of the invention further comprises a first sensor element 603 for measuring the first signal indicative of cardiovascular motion from individual's body 609. The sensor element 603 may comprise, for example, an accelerometer, a piezoelectronic sensor, or any other element suitable for measuring force, acceleration, displacement, or any other physical quantity related to and indicative of cardiovascular motion. The sensor element may further comprise, for example, an amplifier, a signal filter, and/or an analog-to-digital "AD" converter. An accelerometer is advantageously a three-axis accelerometer which is capable of measuring movements independently in three mutually orthogonal directions x, y, and z of e.g. the coordinate system 650 shown in FIG. 6. In this case, the first signal indicative of cardiovascular motion comprises three components and the first signal can be, for example, pre-processed by forming its Euclidian norm, i.e. the absolute value of the three component vector indicative of cardiovascular motion.

The sensor element 603 is connected to the signal interface 601 via one or more data transfer links each of which can be, for example, a radio link or a corded link.

The data transfer from the sensor element 603 to the signal interface 601 may take place either directly or via a data transfer network 605 such as e.g. a telecommunications network. In the exemplifying case shown in FIG. 6, the sensor element 603 is connected to a radio transmitter 608. It is also possible that the apparatus comprising the processing device 602 is integrated with the sensor elements. In this case, the signal interface is actually a simple wiring from the sensor element 603 to the processing device 602.

An apparatus according to an exemplifying embodiment of the invention further comprises a second sensor element 604 for measuring, from the individual's body 609, the second signal indicative of electromagnetic phenomena related to cardiac activity. In this exemplifying case, the sensor element 604 comprises electrodes suitable for being attached to individual's body. The sensor element 604 may further comprise, for example, an amplifier, a signal filter, and/or an analog-to-digital "AD" converter. The second signal measured with the sensor element 604 can be delivered to the signal interface 601 with the aid of the same data transfer means as the first signal measured with the sensor element 603.

An apparatus according to an exemplifying embodiment of the invention is configured to record the first signal and/or the second signal measured within a time window having a fixed temporal start point and a fixed temporal end point or within a sliding time window having a fixed temporal length and moving along with elapsing time. The apparatus may comprise an internal memory 607 for recording the first and/or second signals and/or the apparatus may comprise a data port for connecting to an external memory.

An apparatus according to an exemplifying embodiment of the invention comprises means for pre-processing the first signal indicative of cardiovascular motion and/or the second signal indicative of electromagnetic phenomena related to cardiac activity. The pre-processing may comprise, for example, cancellation of noise on the first signal caused by e.g. breathing, non-cardiovascular movements of an individual, tremble caused by external reasons, etc. The means for pre-processing can be, for example, implemented with the processing device 602 or there can be one or more separate processing devices for the pre-processing.

The processing device 602 can be, for example, implemented with one or more processor circuits, each of which can be a programmable processor circuit provided with appropriate software, a dedicated hardware processor such as, for example, an application specific integrated circuit "ASIC", or a configurable hardware processor such as, for example, a field programmable gate array "FPGA".

An apparatus according to an exemplifying embodiment of the invention is a portable system including the first sensor element 603, the processing device 602 connected to the first sensor element 603, and an appropriate signal interface and/or a user interface for outputting a signal expressing cardiac malfunction when the cardiac malfunction takes place. For example, an apparatus according to an exemplifying embodiment of the invention can be integrated with a portable electrocardiography "ECG" device so that the portable ECG device is provided with the first sensor element 603 for measuring the first signal indicative of cardiovascular motion. A processing system of the portable ECG device can be configured to detect whether a time-trend of the first signal manifests an indicative phenomenon where an amplitude of a first heartbeat is greater than an amplitude of a second heartbeat and a heartbeat rate is greater prior to the first heartbeat than prior to the second heartbeat, and to produce an indicator of cardiac malfunction in response to detection of the indicative phenomenon.

An apparatus according to an exemplifying embodiment of the invention is a wearable system that may comprise for example a vest or another piece of clothing including the first sensor element 603, the processing device 602 connected to the first sensor element 603, and an appropriate signal interface and/or a user interface for outputting a signal expressing cardiac malfunction when the cardiac malfunction takes place.

The first sensor element 603 can be a micro-electro-mechanical system "MEMS" which makes it possible that the size of the apparatus according to an exemplifying embodiment of the invention can be small. It is also possible that the apparatus is an implantable, i.e. under-skin, apparatus. An apparatus according to this exemplifying embodiment of the invention can be for example integrated with an under-skin cardiac monitoring system such as e.g. Reveal LINQ™ of Medtronic. The apparatus is implanted on the chest region.

Furthermore, an apparatus according to an exemplifying embodiment of the invention can be implemented with a programmable mobile phone or other mobile device which comprises an acceleration sensor suitable for producing the first signal indicative of cardiovascular motion. The apparatus according to this exemplifying embodiment of the invention can be implemented by programming the mobile phone or other mobile device to detect whether a time-trend of the first signal manifests an indicative phenomenon where an amplitude of a first heartbeat is greater than an amplitude of a second heartbeat and a heartbeat rate is greater prior to the first heartbeat than prior to the second heartbeat, and to produce an indicator of cardiac malfunction in response to detection of the indicative phenomenon. The apparatus implemented with the mobile phone or other mobile device can be used by placing the apparatus on or against the chest of an individual under consideration.

The specific examples provided in the description given above should not be construed as limiting the scope and/or the applicability of the appended claims. Furthermore, it is also to be noted that, in many cases, the present invention can be used together with other techniques for detecting cardiac malfunctions.

What is claimed is:
1. An apparatus comprising:
  a signal interface configured to receive a first signal indicative of cardiovascular motion; and
  a processing device coupled to the signal interface, the processing device being configured to:
    determine, based on the first signal, a correlation between amplitudes of heartbeats and quantities indicative of heartbeat rates prior to the heartbeats to detect whether a time-trend of the first signal manifests an indicative phenomenon where an amplitude of a first heartbeat is greater than an amplitude of a second heartbeat and a heartbeat rate is greater prior to the first heartbeat than prior to the second heartbeat,
    produce an indicator of cardiac malfunction in response to detection of the indicative phenomenon, and
    output the indicator to a user to treat or diagnose a patient.
2. The apparatus according to claim 1, wherein the processing device is configured to use a temporal length of a heartbeat period preceding the first heartbeat as a quantity indicative of the heartbeat rate prior to the first heartbeat, and a temporal length of a heartbeat period preceding the second heartbeat as a quantity indicative of the heartbeat rate prior to the second heartbeat.

3. The apparatus according to claim 1, wherein the processing device is configured to determine the correlation between the amplitudes of the heartbeats and temporal lengths of the heartbeat periods preceding the heartbeats, a negative correlation indicating presence of the indicative phenomenon.

4. The apparatus according to claim 1, wherein the processing device is configured to determine the correlation between the amplitudes of the heartbeats and heartbeat rates on heartbeat periods preceding the heartbeats, a positive correlation indicating presence of the indicative phenomenon.

5. The apparatus according to claim 1, wherein the processing device is configured to compute a correlation coefficient C indicative of the degree of the correlation between the amplitudes of the heartbeats and the quantities indicative of the heartbeat rates prior to the heartbeats:

$$C=E\{(A-\mu_A)\times(Q-\mu_Q)\},$$

where E is the expected value operator, A represents the amplitudes of the heartbeats, $m_A$ is the mean of the amplitudes, Q represents the quantities indicative of the heartbeat rates, and $m_Q$ is the mean of the quantities indicative of the heartbeat rates.

6. The apparatus according to claim 1, wherein the processing device is configured to extract or produce, from or on the basis of the first signal, one of the following which represent the amplitudes of the heartbeats: heights of AO-peaks caused by opening of the aortic valve, maximum peak-to-peak values within time windows each involving one of the AO-peaks, root-mean-square values computed over the time windows each involving one of the AO-peaks.

7. The apparatus according to claim 6, wherein the processing device is configured to extract, from the first signal, time periods between successive AO-peaks, temporal lengths of the time periods between successive AO-peaks being indicative of the heartbeat rates prior to the heartbeats.

8. The apparatus according to claim 6, wherein the signal interface is configured to receive a second signal indicative of electromagnetic phenomena related to cardiac activity, and the processing device is configured to extract, from the second signal, time periods between successive R-peaks, the R-peaks being caused by depolarization of the ventricular muscle tissue and temporal lengths of the time periods between the successive R-peaks being indicative of the heartbeat rates prior to the heartbeats.

9. The apparatus according to claim 1, wherein the processing device is configured to determine time variation indicative of variation of the temporal lengths of the heartbeat periods and to detect whether the time-trend of the first signal manifests the indicative phenomenon in response to a situation in which the detected time variation exceeds a threshold.

10. The apparatus according to claim 9, wherein the processing device is configured to determine a variation-quantity V indicative of the time variation:

$$V = \frac{\sqrt{E\{(TL-\mu_T)^2\}}}{\mu_T},$$

where E is the expected value operator, TL represents the temporal lengths of the heartbeat periods, and $m_T$ is the mean of the temporal lengths of the heartbeat periods.

11. The apparatus according to claim 1, further comprising a sensor element configured to measure the first signal.

12. The apparatus according to claim 11, wherein the sensor element comprises one of the following: an accelerometer and a piezo-electronic sensor.

13. The apparatus according to claim 11, wherein the sensor element is a micro-electro-mechanical system.

14. The apparatus according to claim 11, wherein the apparatus is implantable under a skin of an individual under consideration.

15. The apparatus according to claim 11, wherein the apparatus is a mobile phone comprising the sensor element and the processing device.

16. The apparatus according to claim 11, wherein the apparatus is wearable and comprises a piece of clothing including the sensor element and the processing device connected to the sensor element.

17. The apparatus according to claim 1, wherein the processing device is configured to produce a signal expressing atrial fibrillation in response to a situation in which the indicative phenomenon is detected to be present.

18. A method comprising:
    determining, based on a first signal indicative of cardiovascular motion, a correlation between amplitudes of heartbeats and quantities indicative of heartbeat rates prior to the heartbeats to detect whether a time-trend of the first signal manifests an indicative phenomenon where an amplitude of a first heartbeat is greater than an amplitude of a second heartbeat and a heartbeat rate is greater prior to the first heartbeat than prior to the second heartbeat;
    producing an indicator of cardiac malfunction in response to detection of the indicative phenomenon; and
    outputting the indicator to a user to treat or diagnose a patient.

19. The method according to claim 18, wherein a temporal length of a heartbeat period preceding the first heartbeat is used as a quantity indicative of the heartbeat rate prior to the first heartbeat, and a temporal length of a heartbeat period preceding the second heartbeat is used as a quantity indicative of the heartbeat rate prior to the second heartbeat.

20. The method according to claim 18, further comprising:
    determining the correlation between the amplitudes of the heartbeats and temporal lengths of the heartbeat periods preceding the heartbeats, a negative correlation indicating existence of the indicative phenomenon.

21. The method according to claim 18, further comprising:
    determining the correlation between the amplitudes of the heartbeats and heartbeat rates on heartbeat periods preceding the heartbeats, a positive correlation indicating existence of the indicative phenomenon.

22. The method according to claim 18, further comprising:
    computing a correlation coefficient C indicative of the degree of the correlation between the amplitudes of the heartbeats and the quantities indicative of the heartbeat rates prior to the heartbeats:

$$C=E\{(A-\mu_A)\times(Q-\mu_Q)\},$$

where E is the expected value operator, A represents the amplitudes of the heartbeats, $m_A$ is the mean of the amplitudes, Q represents the quantities indicative of the heartbeat rates, and $m_Q$ is the mean of the quantities indicative of the heartbeat rates.

23. The method according to claim 18, further comprising:
   extracting or producing, from or on the basis of the first signal, one of the following which represent the amplitudes of the heartbeats: heights of AO-peaks caused by opening of the aortic valve, maximum peak-to-peak values within time windows each involving one of the AO-peaks, root-mean-square values computed over the time windows each involving one of the AO-peaks.

24. The method according to claim 23, further comprising:
   extracting, from the first signal, time periods between successive AO-peaks, temporal lengths of the time periods between successive AO-peaks being indicative of the heartbeat rates prior to the heartbeats.

25. The method according to claim 23, further comprising:
   extracting, from a second signal indicative of electromagnetic phenomena related to cardiac activity, time periods between successive R-peaks, the R-peaks being caused by depolarization of the ventricular muscle tissue and temporal lengths of the time periods between the successive R-peaks being indicative of the heartbeat rates prior to the heartbeats.

26. The method according to claim 18, further comprising:
   determining time variation indicative of variation of the temporal lengths of the heartbeat periods and to detect whether the time-trend of the first signal manifests the indicative phenomenon in response to a situation in which the detected time variation exceeds a threshold.

27. The method according to claim 26, further comprising:
   determining a variation-quantity V indicative of the time variation:

$$V = \frac{\sqrt{E\{(TL - \mu_T)^2\}}}{\mu_T},$$

where E is the expected value operator, TL represents the temporal lengths of the heartbeat periods, and $m_T$ is the mean of the temporal lengths of the heartbeat periods.

28. The method according to claim 18, further comprising:
   producing a signal expressing atrial fibrillation in response to a situation in which the indicative phenomenon is detected to be present.

29. A non-transitory computer-readable medium on which is stored a computer program which comprises computer executable instructions for controlling a programmable processor to:
   determine, based on a first signal indicative of cardiovascular motion, a correlation between amplitudes of heartbeats and quantities indicative of heartbeat rates prior to the heartbeats to detect whether a time-trend of the first signal manifests an indicative phenomenon where an amplitude of a first heartbeat is greater than an amplitude of a second heartbeat and a heartbeat rate is greater prior to the first heartbeat than prior to the second heartbeat;
   produce an indicator of cardiac malfunction in response to detection of the indicative phenomenon; and
   output the indicator to a user to treat or diagnose a patient.

* * * * *